United States Patent
Mao et al.

(10) Patent No.: US 12,193,467 B2
(45) Date of Patent: Jan. 14, 2025

(54) METHODS FOR PREVENTING CRYSTAL MALTITOL FROM CAKING IN STORAGE

(71) Applicant: ZHEJIANG HUAKANG PHARMACEUTICAL CO., LTD., Zhejiang (CN)

(72) Inventors: Baoxing Mao, Quzhou (CN); Ling Wan, Quzhou (CN); Jingjing Xu, Quzhou (CN); Zhihui Yao, Quzhou (CN); Bo Xu, Quzhou (CN); Hang Yue, Quzhou (CN); Fuan Wan, Quzhou (CN)

(73) Assignee: ZHEJIANG HUAKANG PHARMACEUTICAL CO., LTD., Quzhou (CN)

( * ) Notice: Subject to any disclaimer, the term of this patent is extended or adjusted under 35 U.S.C. 154(b) by 0 days.

(21) Appl. No.: 18/656,578

(22) Filed: May 6, 2024

(65) Prior Publication Data

US 2024/0284943 A1    Aug. 29, 2024

Related U.S. Application Data

(63) Continuation of application No. PCT/CN2023/102135, filed on Jun. 25, 2023.

(30) Foreign Application Priority Data

Jul. 9, 2022 (CN) .......................... 202210807761.2

(51) Int. Cl.
| | | |
|---|---|---|
| A23L 3/40 | (2006.01) | |
| A23L 27/30 | (2016.01) | |
| C07H 1/06 | (2006.01) | |
| C07H 15/04 | (2006.01) | |
| G01D 21/02 | (2006.01) | |
| G01D 1/06 | (2006.01) | |

(52) U.S. Cl.
CPC ................. A23L 3/40 (2013.01); A23L 27/34 (2016.08); C07H 1/06 (2013.01); C07H 15/04 (2013.01); G01D 21/02 (2013.01)

(58) Field of Classification Search
CPC .. A23L 3/40; A23L 27/34; C07H 1/06; C07H 15/04; G01D 21/02; A23V 2250/6416; A23V 2300/10
USPC ........................................................ 127/63
See application file for complete search history.

(56) References Cited

U.S. PATENT DOCUMENTS

| 4,816,445 A | 3/1989 | Mitsuhashi et al. |
|---|---|---|
| 2008/0097085 A1* | 4/2008 | Sano ....................... A23L 29/37 |
| | | 536/4.1 |
| 2009/0204246 A1* | 8/2009 | Boder .................. G05B 13/048 |
| | | 700/103 |
| 2011/0027355 A1* | 2/2011 | Lefevre .................... A23G 3/42 |
| | | 426/321 |

FOREIGN PATENT DOCUMENTS

| CN | 101018798 A | 8/2007 |
|---|---|---|
| CN | 101990426 A | 3/2011 |
| CN | 114084525 A | 2/2022 |
| CN | 115053943 A | 9/2022 |
| TH | 112534 A | 2/2012 |

OTHER PUBLICATIONS

International Search Report in PCT/CN2023/102135 mailed on Sep. 11, 2023, 9 pages.
Written Opinion in PCT/CN2023/102135 mailed on Sep. 11, 2023, 6 pages.
Wang, Zenghui et al., Discussion on the technology of refined sugar curing silo, Hoisting and Conveying Machinery, 2019, 4 pages.

* cited by examiner

*Primary Examiner* — Coris Fung
*Assistant Examiner* — Ritu S Shirali
(74) *Attorney, Agent, or Firm* — METIS IP LLC

(57) ABSTRACT

A method for preventing crystal maltitol from caking in storage, comprising: detecting a temperature and a humidity of a dried crystal maltitol on-line in real time, an on-line temperature and humidity meter being configured to set a sieving and packaging treatment condition, a redrying treatment condition, and an aging treatment condition; performing a sieving and packaging treatment on the crystal maltitol whose temperature and humidity satisfy the sieving and packaging treatment condition, performing a redrying treatment or an aging treatment on the crystal maltitol whose temperature and humidity satisfy the redrying treatment condition or the aging treatment condition; detecting a temperature and a humidity of the crystal maltitol after the redrying treatment or the aging treatment, and performing the sieving and packaging treatment on the crystal maltitol whose temperature and humidity satisfy the sieving and packaging treatment condition, or else continuing with the redrying treatment or the aging treatment.

1 Claim, No Drawings

METHODS FOR PREVENTING CRYSTAL MALTITOL FROM CAKING IN STORAGE

CROSS-REFERENCE TO RELATED APPLICATIONS

This application is a Continuation of International Application No. PCT/CN2023/102135, filed on Jun. 25, 2023, which claims priority to Chinese Patent Application No. 202210807761.2, filed on Jul. 9, 2022, the entire contents of each of which are hereby incorporated by reference.

TECHNICAL FIELD

The present disclosure relates to the technical field of sugar alcohol storage, and particularly relates to a method for preventing crystal maltitol from caking in storage.

BACKGROUND

Maltitol, with molecular formula $C_{12}H_{24}O_{11}$, is functional sugar alcohol, generally made from maltose by hydrogenation, decolorization, and crystallization, with characteristics such as high sweetness, high stability, low calorie, non-cariogenicity, as well as a strong hygroscopicity.

At present, the production process of preparing crystal maltitol is mainly to make maltose syrup from starch through liquefaction and saccharification, and then hydrogenate the maltose syrup under a high temperature and a high pressure to make maltitol liquid, and finally make the crystal maltitol through refining processes such as decolorization, crystallization, centrifugation, and drying. Crystal maltitol made by this process has a high risk of caking when stored due to the high moisture and fine particle size of the crystal itself, combined with conditions such as being squeezed or high ambient temperature and humidity. Maltitol usually forms pseudo-caking in about 6 months. This kind of caking may be re-broken with a small amount of external force. However, over time, when the storage time exceeds 1 year without any treatment measures, the pseudo-caking may evolve into the real caking. The real caking of the crystal maltitol, difficult to be broken, difficult to transport through equipment, is not conducive to industrial use, and can only be treated as re-dissolved products or end-of-life products, which increases production costs and wastes resources.

Therefore, it is desired to propose a method for preventing crystal maltitol from caking in storage to avoid caking in the storage process of crystal maltitol, thereby avoiding a waste of resources.

SUMMARY

Embodiments of the present disclosure provide a method for preventing crystal maltitol from caking in storage, comprising: temporarily storing dried crystal maltitol in a storage tank, wherein the storage tank is provided with an on-line temperature and humidity meter, the on-line temperature and humidity meter being configured to set a sieving and packaging treatment condition, a redrying treatment condition, and an aging treatment condition; the sieving and packaging treatment condition includes that: a temperature of the crystal maltitol is less than 20° C. and a humidity of the crystal maltitol is less than 70% relative humidity (RH); the redrying treatment condition includes that: the temperature of the crystal maltitol is less than 20° C. and the humidity of the crystal maltitol is between 70% RH and 80% RH, or the temperature of the crystal maltitol is between 20° C. and 25° C. and the humidity of the crystal maltitol is less than 80% RH; and the aging treatment condition includes that: the temperature of the crystal maltitol is larger than 25° C. regardless of the humidity of the crystal maltitol, or, the humidity is larger than 80% RH regardless of the temperature of the crystal maltitol.

The temperature and the humidity of the dried crystal maltitol is detected, a sieving and packaging treatment on the crystal maltitol whose temperature and humidity satisfy the sieving and packaging treatment condition is performed, and a redrying treatment or an aging treatment on the crystal maltitol whose temperature and humidity satisfy the redrying treatment condition or the aging treatment condition is performed.

A temperature and a humidity of the crystal maltitol after the redrying treatment or the aging treatment is detected, and the sieving and packaging treatment on the crystal maltitol after the crystal maltitol whose temperature and humidity satisfy the sieving and packaging treatment condition is performed, or the redrying treatment or the aging treatment until the crystal maltitol satisfies the sieving and packaging treatment condition and then performing the sieving and packaging treatment is continued.

The sieving and packaging treatment of the crystal maltitol includes: sieving, with a flow rate of the crystal maltitol at 0 to 3 tons per hour (t/h) the crystal maltitol through a sieving machine including a sieving mesh with a mesh number of 5 to 20; selecting the crystal maltitol passing through the sieving mesh as qualified crystal maltitol with a qualified particle size; and sealing and packaging the qualified crystal maltitol for further long-term storage.

The redrying treatment of the crystal maltitol includes: drying the crystal maltitol through a drying machine, wherein a hot inlet air temperature of the drying machine is from 80 to 90° C., a cold inlet air temperature is less than 20° C., and a flow rate of the crystal maltitol in the redrying treatment is 0 to 3 t/h.

The aging treatment of the crystal maltitol includes: performing the aging treatment, wherein an inlet air temperature is less than 15° C., an inlet air humidity is less than 20%, and a flow rate of the crystal maltitol in the aging treatment is 0 to 3 t/h.

DETAILED DESCRIPTION

In order to make the technical problems, technical solutions and beneficial effects to be solved by the present disclosure clearer and more understandable, the present disclosure is described in further detail hereinafter in combination with the accompanying drawings and embodiments. It should be understood that the specific embodiments described herein are only for explaining the present disclosure and are not intended to limit the present disclosure.

To address the problem of caking of crystal maltitol, practitioners reduce the risk of caking of crystal maltitol by redrying or aging the crystal maltitol product beforehand. However, there is a lack of methods for determining the caking tendency of crystal maltitol. If all crystal maltitol products are subjected to redrying or aging treatment, this will also increase production costs and reduce production efficiency.

The present disclosure provides a method for preventing crystal maltitol from caking in storage, comprising temporarily storing dried crystal maltitol in a storage tank, wherein the storage tank is provided with an on-line temperature and humidity meter, the on-line temperature and humidity meter being configured to set a sieving and packaging treatment condition, a redrying treatment condition, and an aging treatment condition In some embodiments, the sieving and packaging treatment condition includes that: a temperature of the crystal maltitol is less than 20° C. and a humidity of the crystal maltitol is less than 70% RH. The condition is suitable for the dried crystal maltitol with low temperature and humidity.

In some embodiments, the redrying treatment condition includes that: the temperature of the crystal maltitol is less than 20° C. and the humidity of the crystal maltitol is between 70% RH and 80% RH, or the temperature of the crystal maltitol is between 20° C. and 25° C. and the humidity of the crystal maltitol is less than 80% RH. The condition is suitable for the dried crystal maltitol with high temperature and humidity.

In some embodiments, the aging treatment condition includes that: the temperature of the crystal maltitol is larger than 25° C. regardless of the humidity of the crystal maltitol, or, the humidity is larger than 80% RH regardless of the temperature of the crystal maltitol. The condition is suitable for the dried crystal maltitol with both high temperature and humidity.

The temperature of the crystal maltitol is a temperature of the crystal maltitol in the storage tank measured by the on-line temperature and humidity meter. The humidity of the crystal maltitol is a temperature of the crystal maltitol in the storage tank measured by the on-line temperature and humidity meter.

Based on the above temperature and humidity conditions, Table 1 corresponding to the treatment method was obtained.

TABLE 1

A correspondence between temperature/humidity of dried crystal maltitol and the treatment method

| | Temperature (° C.) | | | |
|---|---|---|---|---|
| Treatment method | <15 | 15~20 | 20~25 | >25 |
| Humidity (% RH) | <60 | sieving and packaging treatment | | |
| | 60~70 | | | |
| | 70~80 | redrying treatment | | |
| | >80 | aging treatment | | |

The temperature and the humidity of the dried crystal maltitol is detected, a sieving and packaging treatment on the crystal maltitol whose temperature and humidity satisfy the sieving and packaging treatment condition is performed, and a redrying treatment or an aging treatment on the crystal maltitol whose temperature and humidity satisfy the redrying treatment condition or the aging treatment condition is performed.

A temperature and a humidity of the crystal maltitol after the redrying treatment or the aging treatment is detected, and the sieving and packaging treatment on the crystal maltitol after the crystal maltitol whose temperature and humidity satisfy the sieving and packaging treatment condition is performed, or the redrying treatment or the aging treatment until the crystal maltitol satisfies the sieving and packaging treatment condition and then performing the sieving and packaging treatment is continued.

In some embodiments, the sieving and packaging treatment of the crystal maltitol includes: sieving, with a flow rate of the crystal maltitol at 0 to 3 tons per hour (t/h) the crystal maltitol through a sieving machine including a sieving mesh with a mesh number of 5 to 20; selecting the crystal maltitol passing through the sieving mesh as qualified crystal maltitol with a qualified particle size; and sealing and packaging the qualified crystal maltitol for further long-term storage.

In some embodiments, the redrying treatment of the crystal maltitol includes: drying the crystal maltitol through a drying machine, wherein a hot inlet air temperature of the drying machine is from 80 to 90° C., a cold inlet air temperature is less than 20° C., and a flow rate of the crystal maltitol in the redrying treatment is 0 to 3 t/h.

In some embodiments, the aging treatment of the crystal maltitol includes: performing the aging treatment, wherein an inlet air temperature is less than 15° C., an inlet air humidity is less than 20%, and a flow rate of the crystal maltitol in the aging treatment is 0 to 3 t/h.

By monitoring the temperature and humidity of the crystal maltitol in real time, the crystal maltitol that satisfies the sieving and packaging treatment condition is directly screened and packaged, and the crystal maltitol that does not satisfy the sieving and packaging treatment condition is first subjected to the redrying treatment or aging until the sieving and packaging treatment condition are met and then packaged, so as to categorize the crystal maltitol in different temperature and humidity condition, effectively prevent the storage of crystal maltitol from caking, and avoid the wastage of resources.

The method of the present disclosure for preventing crystal maltitol from caking in storage is further described below in connection with specific embodiments.

Embodiment 1

A first embodiment of the method for preventing crystal maltitol from caking in storage of the present disclosure includes the following operations.

In operation 11, a maltose syrup liquid with a refractive index in a range from 50 to 60% was obtained by saccharifying and liquefying the starch. The maltose syrup was hydrogenated under following condition. A reaction temperature was less than 145° C.; a reaction pressure was in a range from 6.5 to 9.5 Mpa; a reaction time was in a range from 110 to 180 min to obtain a maltitol liquid. The maltitol liquid was decolorized and exchanged to obtain a refined liquid with a pH of 3.5 to 7.5 and a conductivity less than 30 µS/cm. The refined maltitol liquid was evaporated and concentrated to obtain a concentrated liquid with a refractive index of 75 to 85%. The concentrated liquid was crystallized and dried to obtain the dried crystal maltitol.

In operation 12, temperature and humidity data of the dried crystal maltitol was detected by an on-line temperature and humidity meter. The temperature of the dried crystal maltitol was less than 20° C., and the humidity was less than 70% RH, which were in line with the sieving and packaging treatment condition.

In operation 13, the dried crystal maltitol was directly sieved and packaged. The crystal maltitol was screened by a sieving machine installed with a 10-mesh mesh screen, a flow rate of the crystal maltitol was controlled at 0 to 3 t/h, and screened material was selected as particle size-qualified crystal maltitol products to be sealed and packaged and then stored for a long period of time, and the caking of the products was regularly detected and recorded, and detection results are shown in Table 2.

Embodiment 2

A second embodiment of the method for preventing crystal maltitol from caking in storage of the present disclosure includes the following operations.

In operation 21, a maltose syrup liquid with a refractive index in a range from 50 to 60% was obtained by saccharifying and liquefying the starch. The maltose syrup was hydrogenated under following conditions. A reaction temperature was less than 145° C.; a reaction pressure was in a range from 6.5 to 9.5 Mpa; a reaction time was in a range from 110 to 180 min to obtain a maltitol liquid. The maltitol liquid was decolorized and exchanged to obtain a refined liquid with a pH of 3.5 to 7.5 and a conductivity less than 30 μS/cm. The refined maltitol liquid was evaporated and concentrated to obtain a concentrated liquid with a refractive index of 75 to 85%. The concentrated liquid was crystallized and dried to obtain the dried crystal maltitol.

In operation 22, temperature and humidity data of the dried crystal maltitol was detected by the on-line temperature and humidity meter. The temperature of the dried crystal maltitol was less than 20° C., and the humidity was larger than 70% RH and less than 80% RH, or the temperature of the dried crystal maltitol was larger than 20° C. and less than 25° C., and the humidity was less than 80% RH, which were in line with the redrying treatment condition.

In operation 23, the redrying treatment was performed on the dried crystal maltitol. The crystal maltitol was dried by the drying machine, a hot air inlet temperature of the drying machine was controlled to be in a range from 80 to 90° C., a cold air inlet temperature was less than 20° C., and a flow rate of the crystal maltitol was in a range from 0 to 3 t/h. The temperature and humidity of the crystal maltitol after the redrying treatment were detected, and when the crystal maltitol met the sieving and packaging condition, the crystal maltitol is conveyed to be screened and packaged again; otherwise, the crystal maltitol continues to perform the redrying treatment or aging treatment.

liquid was decolorized and exchanged to obtain a refined liquid with a pH of 3.5 to 7.5 and a conductivity less than 30 μS/cm. The refined maltitol liquid was evaporated and concentrated to obtain a concentrated liquid with a refractive index of 75 to 85%. The concentrated liquid was crystallized and dried to obtain the dried crystal maltitol.

In operation 32, temperature and humidity data of the dried crystal maltitol was detected by the on-line temperature and humidity meter. A temperature of the dried crystal maltitol was larger than 25° C., regardless of a humidity; or, a humidity was larger than 80% RH, regardless of a temperature, which was in accordance with the aging treatment condition.

In operation 33, the dried crystal maltitol was aged. The crystal maltitol was aged, an inlet air temperature was controlled to be less than 15° C., an inlet air humidity was less than 20%, and a flow rate of the crystal maltitol was in a range from 0 to 3 t/h. The temperature and humidity of the crystal maltitol after the aging treatment were detected, and when the crystal maltitol satisfies the sieving and packaging condition, the crystal maltitol is conveyed to be screened and packaged again; otherwise, the crystal maltitol continues to perform the redrying treatment or the aging treatment.

The crystal maltitol was screened through a sieving machine including a sieving mesh with a mesh number of 20, and a flow rate of the crystal maltitol was controlled at 0 to 3 t/h. The crystal maltitol passing through the sieving mesh was selected as qualified crystal maltitol with a qualified particle size to be sealed and packaged for further long-term storage, and the caking of the products was regularly detected and recorded, and test results are shown in Table 2.

TABLE 2

| | \multicolumn{8}{c|}{Caking of the crystal maltitol products of embodiments 1 to 3} |
|---|---|---|---|---|---|---|---|---|
| | 1 month | 3 months | 6 months | 9 months | 12 months | 15 months | 18 months | 24 months |
| Embodiment 1 | Un-caking | Un-caking | Un-caking | Un-caking | Un-caking | Un-caking | Un-caking | Un-caking |
| Embodiment 2 | Un-caking | Un-caking | Un-caking | Un-caking | Un-caking | Un-caking | Un-caking | Un-caking |
| Embodiment 3 | Un-caking | Un-caking | Un-caking | Un-caking | Un-caking | Un-caking | Un-caking | Un-caking |

The crystal maltitol was screened through a sieving machine installed with a 5-mesh screen, and a flow rate of the crystal maltitol was controlled at 0 to 3 t/h. Screened material was selected as particle size-qualified crystal maltitol products to be sealed and packaged for further long-term storage, and the caking of the products was regularly detected and recorded, and test results are shown in Table 2.

Embodiment 3

A third embodiment of the method for preventing crystal maltitol from caking in storage of the present disclosure includes the following operations.

In operation 31, a maltose syrup liquid with a refractive index in a range from 50 to 60% was obtained by saccharifying and liquefying the starch. The maltose syrup was hydrogenated under following conditions. A reaction temperature was less than 145° C.; a reaction pressure was in a range from 6.5 to 9.5 Mpa; a reaction time was in a range from 110 to 180 min to obtain a maltitol liquid. The maltitol It can be seen that a storage period of the crystal maltitol products prepared by the technical solution of the present disclosure without caking is not shorter than 24 months.

The foregoing is only preferred embodiments of the present disclosure, and is not intended to limit the present disclosure, and any modifications, equivalent substitutions, improvements, etc. made within the spirit and principles of the present disclosure shall be included in the scope of protection of the present disclosure.

What is claimed is:
1. A method for preventing crystal maltitol from caking in storage, comprising:
temporarily storing dried crystal maltitol in a storage tank, wherein
the storage tank is provided with an on-line temperature and humidity meter, the on-line temperature and humidity meter being configured to set a sieving and packaging treatment condition, a redrying treatment condition, and an aging treatment condition;

the sieving and packaging treatment condition includes that: a temperature of the dried crystal maltitol is less than 20° C. and a humidity of the dried crystal maltitol is less than 70% relative humidity (RH);

the redrying treatment condition includes that: the temperature of the dried crystal maltitol is less than 20° C. and the humidity of the dried crystal maltitol is between 70% RH and 80% RH, or the temperature of the dried crystal maltitol is between 20° C. and 25° C. and the humidity of the dried crystal maltitol is less than 80% RH; and the aging treatment condition includes that: the temperature of the dried crystal maltitol is larger than 25° C. regardless of the humidity of the dried crystal maltitol, or, the humidity is larger than 80% RH regardless of the temperature of the dried crystal maltitol;

detecting the temperature and the humidity of the dried crystal maltitol;

performing a sieving and packaging treatment on the dried crystal maltitol whose temperature and humidity satisfy the sieving and packaging treatment condition;

performing a redrying treatment or an aging treatment on the dried crystal maltitol whose temperature and humidity satisfy the redrying treatment condition or the aging treatment condition;

detecting a temperature and a humidity of the dried crystal maltitol after the redrying treatment or the aging treatment; and performing the sieving and packaging treatment on the dried crystal maltitol after the dried crystal maltitol whose temperature and humidity satisfy the sieving and packaging treatment condition, or else continuing with the redrying treatment or the aging treatment until the dried crystal maltitol satisfies the sieving and packaging treatment condition and then performing the sieving and packaging treatment; wherein, the sieving and packaging treatment of the dried crystal maltitol includes:
  sieving, with a flow rate of the dried crystal maltitol at 0 to 3 tons per hour (t/h) the dried crystal maltitol through a sieving machine including a sieving mesh with a mesh number of 5 to 20;
  selecting the dried crystal maltitol passing through the sieving mesh as qualified crystal maltitol with a qualified particle size; and
  sealing and packaging the qualified crystal maltitol for further long-term storage;

the redrying treatment of the dried crystal maltitol includes:
  drying the dried crystal maltitol through a drying machine, wherein a hot inlet air temperature of the drying machine is from 80 to 90° C., a cold inlet air temperature is less than 20° C., and a flow rate of the dried crystal maltitol in the redrying treatment is 0 to 3 t/h; and the aging treatment of the dried crystal maltitol includes:
  performing the aging treatment, wherein an inlet air temperature is less than 15° C., an inlet air humidity is less than 20%, and a flow rate of the dried crystal maltitol in the aging treatment is 0 to 3 t/h.

* * * * *